(12) United States Patent
Perrin et al.

(10) Patent No.: US 8,673,308 B2
(45) Date of Patent: Mar. 18, 2014

(54) TARGETING OF CD8+ T-LYMPHOCYTES TO TREAT NEURODEGENERATIVE DISEASES

(75) Inventors: Steven Perrin, Newbury, MA (US); John Lincecum, Jamaica Plain, MA (US); Alan Gill, Reading, MA (US); Fernando Vieira, Boston, MA (US)

(73) Assignee: ALS Therapy Development Institute, Cambridge, MA (US)

( * ) Notice: Subject to any disclaimer, the term of this patent is extended or adjusted under 35 U.S.C. 154(b) by 0 days.

(21) Appl. No.: 13/403,379

(22) Filed: Feb. 23, 2012

(65) Prior Publication Data

US 2012/0237505 A1 Sep. 20, 2012

Related U.S. Application Data

(60) Provisional application No. 61/445,666, filed on Feb. 23, 2011.

(51) Int. Cl.
*A61K 38/00* (2006.01)
*A61K 39/395* (2006.01)

(52) U.S. Cl.
USPC .................. 424/154.1; 424/130.1; 424/144.1; 514/17.7

(58) Field of Classification Search
None
See application file for complete search history.

(56) References Cited

U.S. PATENT DOCUMENTS

| | | | |
|---|---|---|---|
| 5,604,229 | A | 2/1997 | Fujita et al. |
| 7,456,157 | B2 | 11/2008 | Kohno et al. |
| 2005/0090520 | A1 | 4/2005 | Lindquist |
| 2005/0282766 | A1* | 12/2005 | Wu et al. .......................... 514/44 |
| 2008/0138333 | A1* | 6/2008 | Hansen et al. ............. 424/133.1 |
| 2009/0176744 | A1 | 7/2009 | Liu et al. |

FOREIGN PATENT DOCUMENTS

WO 2005/025553 A2 3/2005

OTHER PUBLICATIONS

Beers et al. 2008 "CD4+ T cells support glial neuroprotection, slow disease progression, and modify glial morphology in an animal model of inherited ALS" PNAS 105(40):15558-15563.*
Friese and Fugger (2005) "Autoreactive CD8+ T cells in multiple sclerosis: a new target for therapy?" Brain 128:1747-1763.*
Mohan (2009) "Therapeutic implications of variable expression of CD52 on clonal cytotoxic T cells in CD8+ large granular lymphocyte leukemia" haematologica 94(10):1407-1414.*
Willis et al. (2001) "The effect of treatment with Campath-1H in patients with autoimmune cytopenias" British J of Haematology 114:891-898.*
Rafii and Aisen 2009 "Recent developments in Alzheimer's disease therapeutics" BMC Medicine 7(7):1-4.*
Reynolds et al. 2002 "anti-CD8 monoclonal antibody therapy is effective in the prevention and treatment of experimental autoimmune glomerulonephritis" J Am Soc Nephrol 13:359-369.*
[No Author Listed] Gilenya (fingolimod). FDA Label. Approved in 2010. 22 pages.
Anselmo et al., FTY720 pretreatment reduces warm hepatic ischemia reperfusion injury through inhibition of T-lymphocyte infiltration. Am J Transplant. Oct. 2002;2(9):843-9.
Awad et al., Selective sphingosine 1-phosphate 1 receptor activation reduces ischemia-reperfusion injury in mouse kidney. Am J Physiol Renal Physiol. Jun. 2006;290(6):F1516-24. Epub Jan. 10, 2006.
Bolli et al., 2-imino-thiazolidin-4-one derivatives as potent, orally active S1P1 receptor agonists. J Med Chem. May 27, 2010;53(10):4198-211.
Chiu et al., T lymphocytes potentiate endogenous neuroprotective inflammation in a mouse model of ALS. Proc Natl Acad Sci U S A. Nov. 18, 2008;105(46):17913-8. Epub Nov. 7, 2008.
Crosignani et al., Discovery of a novel series of potent S1P1 agonists. Bioorg Med Chem Lett. Mar. 1, 2010;20 (5):1516-9. Epub Jan. 25, 2010.
Dal Canto et al., A low expressor line of transgenic mice carrying a mutant human Cu,Zn superoxide dismutase (SOD1) gene develops pathological changes that most closely resemble those in human amyotrophic lateral sclerosis. Acta Neuropathol. Jun. 1997;93(6):537-50.
Foster et al., Brain penetration of the oral immunomodulatory drug FTY720 and its phosphorylation in the central nervous system during experimental autoimmune encephalomyelitis: consequences for mode of action in multiple sclerosis. J Pharmacol Exp Ther. Nov. 2007;323(2):469-75. Epub Aug. 6, 2007.
Gurney et al., Motor neuron degeneration in mice that express a human Cu,Zn superoxide dismutase mutation. Science. Jun. 17, 1994;264(5166):1772-5.
Miron et al., FTY720 modulates human oligodendrocyte progenitor process extension and survival. Ann Neurol. Jan. 2008;63(1):61-71.
Scott et al., Design, power, and interpretation of studies in the standard murine model of ALS. Amyotroph Lateral Scler. 2008;9(1):4-15.
Sensken et al., Accumulation of fingolimod (FTY720) in lymphoid tissues contributes to prolonged efficacy. J Pharmacol Exp Ther. Mar. 2009;328(3):963-9. Epub Dec. 12, 2008.
Takabe et al., "Inside-out" signaling of sphingosine-1-phosphate: therapeutic targets. Pharmacol Rev. Jun. 2008;60 (2):181-95. Epub Jun. 13, 2008.
Zhang et al., FTY720 ameliorates experimental autoimmune neuritis by inhibition of lymphocyte and monocyte infiltration into peripheral nerves. Exp Neurol. Apr. 2008;210(2):681-90. Epub Jan. 17, 2008.
Zhang et al., Distribution of Foxp3(+) T-regulatory cells in experimental autoimmune neuritis rats. Exp Neurol. Mar. 2009;216(1):75-82. Epub Dec. 3, 2008.

* cited by examiner

*Primary Examiner* — Jeffrey Stucker
*Assistant Examiner* — Adam M Weidner
(74) *Attorney, Agent, or Firm* — Thomas J. Engellenner; Reza Mollaaghababa; Pepper Hamilton LLP

(57) ABSTRACT

Methods and therapeutic agents are disclosed for treating neurodegenerative disorders by depletion of CD8 positive T cells by using antibodies, FAb fragments of antibodies or similar agents that sequester, neutralize or deplete the CD8+ cytotoxic T cells.

17 Claims, 7 Drawing Sheets

TARGETING OF CD8+ T-LYMPHOCYTES TO TREAT NEURODEGENERATIVE DISEASES

CROSS-REFERENCE TO RELATED APPLICATIONS

This application claims priority to U.S. Provisional Application Ser. No. 61/445,666 filed Feb. 23, 2011, herein incorporated by reference in its entirety

BACKGROUND

The present invention relates to the treatment of neurological disorders and, in particular the treatment of neurodegenerative diseases, such as Amyotrophic lateral sclerosis (ALS).

ALS is a progressive neurological disorder characterized by muscle fiber atrophy resulting from the degeneration of motor neurons in the spinal column and brain. ALS affects approximately 30,000 US citizens, with only ≈10% of cases being classified as the familial form of ALS. In a subset of familial patients with mutations in the metabolic enzyme superoxide dismutase 1 (SOD1), the pathological progression may be attributed to an unknown gain of function associated with a mutant form of the enzyme, i.e., is SOD1 dependant. However in the majority of ALS cases the SOD1 gene contains no mutations, the activity of the SOD1 enzyme is normal, and the mechanism of disease pathology is unknown, i.e., not SOD1 dependent. Therefore, the remaining 90% of ALS cases are classified as sporadic cases, with no well-characterized genetic component or causal agent.

Although ALS is characterized by loss of motor neurons in the spinal cord resulting in muscle atrophy, the disease also manifests itself with changes in axon transport, protein aggregation, excitotoxicity, astrocytosis, mitochondrial dysfunction, microglial activation and synaptic remodeling. Microglial activation, astrocytosis and the presence of infiltrating inflammatory cells from outside the central nervous system have been well described. There is accumulation of IgG immunoreactive deposits in the spinal cord of ALS patients, infiltration of lymphocytes, dendritic cells, monocytes, and macrophages into the spinal cord in ALS.

While the role of infiltrating lymphoctyes is poorly understood, recent work suggests that infiltrating T cell populations are neuroprotective. In recent studies mSOD1 mice were crossed with $RAG2^{-/-}$ mice, which have no mature T or B cells, ($mSOD1/RAG2^{-/-}$) or with $CD4^{-/-}$ mice which lack $CD4^+$ T cells. Both the $mSOD1/RAG2^{-/-}$ and $mSOD1/CD4^{-/-}$ transgenic mice have a significantly shorter lifespan (16 vs. 24 weeks) suggesting a neuroprotective effect of infiltrating lymphocytes.

SUMMARY

It has been discovered that certain populations of infiltrating lymphocytes are not neuroprotective but rather are contributing factors in the progression of neurological disorders. In particular, infiltration of CD8-positive (CD8+) T cells have been found to contribute to progressive neurodegeneration, especially in diseases such as Amyotrophic Lateral Sclerosis (ALS). Accordingly, methods and therapeutic agents are disclosed for modulating or ameliorating the neuroinflammatory processes associated with such CD8+ T cell populations in neurodegenerative or neuromuscular disorders. In some embodiments of the present invention this can be achieved through the depletion of CD8+ cytotoxic T cells by using anti-CD8 T cell-depleting antibodies. In some embodiments of the present invention this can be achieved through sequestering, neutralizing or depleting the population of CD8+ cytotoxic T cells by using anti-CD8 T cell-depleting antibodies. In other embodiments, depletion of CD8 positive T cells can be achieved by using FAb fragments of antibodies or similar agents that sequester, neutralize or deplete the CD8+ cytotoxic T cells.

In one aspect of the invention, methods are disclosed for treating a subject for a neurological disorder by administering an agent that depletes CD8+ T cells present in the subject. Preferably, the agent includes an antibody that binds to CD8+ T cells. The antibody can be a full length IgG or a FAb fragment of an antibody. The antibody can also be a human or humanized antibody. The agents or compositions can be administered as a single dose or in multiple doses and can further include a pharmaceutically acceptable diluent, adjuvant, or carrier.

In addition to ALS, CD8+ T cell depletion may also be useful in other neurodegenerative and neuromuscular disorders characterized by activation of antigen-presenting cells or show changes in cytotoxic T cell populations. These indications include, but are not limited to, Alzheimer's Disease, Parkinson's Disease, Myasthenia Gravis, Multifocal Motor Neuropathy, Primary Lateral Sclerosis, Spinal Muscular Atrophy, Kennedy's Disease, and Spinocerebellar Ataxia.

These and other features of the embodiments as will be apparent are set forth and described herein.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

FIGS. 1A and 1B show that anti CD8+ treatment specifically depletes CD8+ T cells and not CD4 T cells from peripheral blood.

Figure 1A:
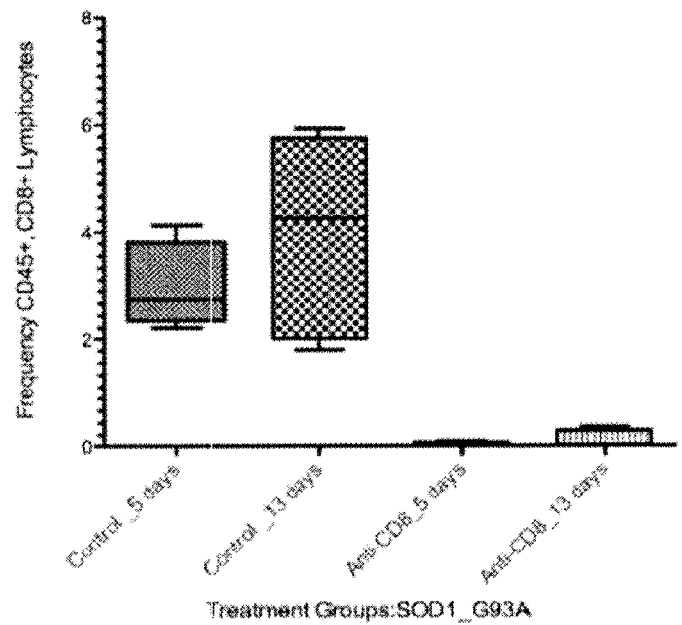
FIG. 1A is a graph of population levels of CD8+ T cells following treatment according to the invention or exposure to control agent only.

It will be understood that the drawings are exemplary only and that all reference to the drawings is made for the purpose of illustration only, and is not intended to limit the scope of the embodiments described herein below in any way.

DETAILED DESCRIPTION

The following abbreviations are used throughout the specifications and known to those skilled in the art: ALS (amyotrophic lateral sclerosis); SOD1 (super oxide dismutase-1); TCR (T cell receptor); MHC (major histocompatibility complex); APC (antigen presenting cell); CD8 (a cell surface antigen on certain T cells), FACS (fluorescence activated cell sorting).

In the description that follows, and in documents incorporated by reference, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent when the promoter is a constitutive promoter.

An isolated DNA molecule is a fragment of DNA that is not integrated in the genomic DNA of an organism. For example, a cloned antibody gene is a DNA fragment that has been separated from the genomic DNA of a mammalian cell. Another example of an isolated DNA molecule is a chemically synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term "expression" refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

As used herein, antibody encompasses naked antibodies and conjugated antibodies and antibody fragments, which may be monospecific or multispecific. It includes recombinant antibodies, such as chimeric antibodies, humanized antibodies and fusion proteins.

A chimeric antibody is a recombinant protein that contains the variable domains and complementary determining regions derived from an animal antibody, such as a rodent antibody, while the remainder of the antibody molecule is derived from a human antibody.

Humanized antibodies are recombinant proteins in which murine complementarity determining regions of a monoclonal antibody have been transferred from heavy and light variable chains of an animal immunoglobulin (such as a murine immunoglobulin) into a human variable domain. A humanized murine antibody (CDR-grafted) has the murine CDRs grafted into the FRs of a human IgG. The CDR-grafted human variable chains are fused to the constant regions of a human antibody to obtain an intact humanized IgG.

Human antibodies are antibodies that either are isolated from humans and then grown out in culture or are made using animals whose immune systems have been altered so that they respond to antigen stimulation by producing human antibodies.

An antibody fragment is a portion of an intact antibody such as $F(ab')_2$, $F(ab)_2$, Fab', Fab, Fv, sFv and the like. Regardless of structure, an antibody fragment binds with the same antigen that is recognized by the full-length antibody. For example, an anti-CD8+ monoclonal antibody fragment binds with an epitope of CD8+ T cells. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

Antibody fragments produced by limited proteolysis of wildtype antibodies are called proteolytic antibody fragments. These include, but are not limited to, the following: $F(ab')_2$ fragments are released from an antibody by limited exposure of the antibody to a proteolytic enzyme, e.g., pepsin or ficin. A F(ab')$_2$ fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes. Fab' fragments contain a single anti-binding domain comprising a Fab and an additional portion of the heavy chain through the hinge region. Fab'-SH fragments are typically produced from F(ab')$_2$ fragments, which are held together by disulfide bond(s) between the H chains in an F(ab')$_2$ fragment. Treatment with a mild reducing agent such as, by way of non-limiting example, beta-mercaptoethylamine, breaks the disulfide bond(s), and two Fab' fragments are released from one F(ab')$_2$ fragment. Fab'-SH fragments are monovalent and monospecific.

Fab fragments (i.e., an antibody fragment that contains the antigen-binding domain and comprises a light chain and part of a heavy chain bridged by a disulfide bond) are produced by papain digestion of intact antibodies. A convenient method is to use papain immobilized on a resin so that the enzyme can be easily removed and the digestion terminated. Fab fragments do not have the disulfide bond(s) between the H chains present in an F(ab')$_2$ fragment.

Single-chain antibodies are one type of antibody fragment. The term single chain antibody is often abbreviated as "scFv" or "sFv." These antibody fragments are produced using molecular genetics and recombinant DNA technology. A single-chain antibody consists of a polypeptide chain that comprises both a $V_H$ and a $V_L$ domain which interact to form an antigen-binding site. The $V_H$ and a $V_L$ domains are usually linked by a peptide of 10 to 25 amino acid residues. The term "single-chain antibody" further includes, but is not limited to, a disulfide-linked Fv (dsFv) in which two single-chain antibodies (each of which may be directed to a different epitope) are linked together by a disulfide bond; a bispecific sFv in which two discrete scFvs of different specificity is connected with a peptide linker; a diabody (a dimerized sFv formed when the $V_H$ domain of a first sFv assembles with the $V_L$ domain of a second sFv and the $V_L$ domain of the first sFv assembles with the $V_H$ domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Thus, when making a scFv, diabody, or triabody, the constant regions are not used, and the humanized variable regions are joined with a linker.

Complementary determining region peptides or CDR peptides are another form of an antibody fragment. A CDR peptide (also known as "minimal recognition unit") is a peptide corresponding to a single complementarity-determining region (CDR), and can be prepared by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106, 1991.

In cysteine-modified antibodies, a cysteine amino acid is inserted or substituted on the surface of antibody by genetic manipulation and used to conjugate the antibody to another molecule via, e.g., a disulfide bridge. Cysteine substitutions or insertions for antibodies have been described (see U.S. Pat. No. 5,219,996). Methods for introducing Cys residues into the constant region of the IgG antibodies for use in site-specific conjugation of antibodies are described by Stimmel et al. (J. Biol. Chem. 275:330445-30450, 2000).

As used herein, a therapeutic conjugate agent is a molecule or atom, which is conjugated to an antibody moiety to produce a conjugate which is useful for therapy. These can be active when given unconjugated to an antibody, such as with $_{131}$I in thyroid neoplasms, and various cytotoxic drugs in cancer, autoimmune diseases, graft versus host disease, and in the immunosuppression induced for organ transplantation, etc. Examples of therapeutic conjugate agents include a therapeutic radionuclide, a boron compound, an immunomodulator, a hormone, a hormone antagonist, an enzyme, oligonucleotides, an enzyme inhibitor, a photoactive therapeutic agent, a cytotoxic agent, and an angiogenesis inhibitor, and a combination thereof, and further described, for example, in US Published Application no. 2004 0057902.

A diagnostic/detection agent is a molecule or atom which is administered conjugated to a multispecific antagonist according to the invention, i.e., antibody or antibody fragment, or subfragment, and is useful in diagnosing a disease by locating the cells containing the antigen. Useful diagnostic/detection agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI), as well as for ultrasound and computed tomography.

A naked antibody is an antibody which is not conjugated with a therapeutic conjugate agent or a dagnostic/detection agent. Naked antibodies include both polyclonal and monoclonal antibodies, as well as certain recombinant antibodies, such as chimeric and humanized antibodies.

A conjugated antibody is an antibody or antibody fragment that is conjugated to a diagnostic or therapeutic conjugate agent. A multispecific antibody is an antibody which can bind simultaneously to at least two targets which are of different structure, e.g., two different antigens, two different epitopes on the same antigen, or a hapten and/or an antigen or epitope. Two or more of the binding arms may be directed to the same or different epitopes of the same antigen, thus constituting multivalency in addition to multispecificity.

A bispecific antibody is an antibody or antibody fragment construct which can bind simultaneously to two targets which are of different structure.

A fusion protein is a recombinantly produced antigen-binding molecule in which two or more different single-chain antibody or antibody fragment segments with the same or different specificities are linked. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

The term "treatment" or "treating" as used herein is intended to encompass preventing the onset, slowing the progression, reversing or otherwise ameliorating a disorder. A disorder includes a condition, such as a neurological condition, an injury (e.g., a spinal cord injury, stroke or a traumatic brain injury) or a disease, such as a neurodegenerative disease (e.g., ALS, Parkinson's disease, Huntington's disease or Alzheimer's disease). An infectious disease is one that is caused by a microbe or parasite. A microbe is a virus, bacteria, rickettsia, mycoplasma, fungi or like microorganisms. A parasite is an infectious, generally microscopic or very small, multicellular invertebrate, protozoan, or an ovum or juvenile form thereof, which is susceptible to antibody-induced clearance or lytic or phagocytic destruction.

The following examples and data demonstrate the presence of CD8 positive T cells in peripheral blood of SOD1$^{G93A}$ animals. Based on FACS analysis, it is further demonstrated that treatment of SOD1$^{G93A}$ animals with a CD8 positive T cell-depleting antibody transiently depletes CD8+ T cells from peripheral blood for up to 28 days, and that anti-CD8 treatment does not deplete CD4+ T cells. In situ hybridization analysis shows that anti-CD8 treatment decreased the expression of activated astrocyte and microglial marker genes (C1qA, lys, Lgals3, Cc13, CD68, CD9) in the spinal cord of SOD1$^{G93A}$ animals.

In the current invention the treatment of hSOD1$^{G93A}$ mice treated with a single bolus injection of anti-CD8 T cell-depleting antibody ablated CD8+ T cell populations without influencing CD4+ T cell populations, and decreased the expression of pro-inflammatory genes in the spinal cord measured 50 days after dosing.

The current invention demonstrates that the treatment of the hSOD1$^{G93A}$ preclinical mouse model with purified NA/LE rat anti-mouse CD8a, clone 53-6.7 (anti-CD8 antibody), an antibody that binds the CD8 antigen on the surface of cytotoxic T cells, trends toward delaying disease onset and prolonging survival in female hSOD1$^{G93A}$ mice.

The clone 53-6.7 anti-CD8 antibody (commercially available from BD Bioscience, San Jose Calif.) has been reported to react with the 38 kDa α and 34 kDa α' chains of the CD8 differentiation antigen (Ly-2 or Lyt-2). The CD8 α and α' chains (CD8a) form heterodimers with the CD8 β chain (CD8b, Ly-3, or Lyt-3) on the surface of CD8+ thymocytes. It has been suggested that the expression of the CD8a/CD8b heterodimer is restricted to T lymphocytes which matured in the thymus or in an extrathymic environment that had been influenced by thymus-initiated neuroendocrine signals. CD8 is an antigen coreceptor on the T-cell surface which interacts with MHC class I molecules on antigen-presenting cells or epithelial cells. It participates in T-cell activation through its association with the T-cell receptor complex and protein tyrosine kinase 1ck (p56 [1ck]). In vivo and in vitro treatment with 53-6.7 mAb has reportedly been effective at depleting CD8+ peripheral T lymphocytes.

Although demonstrated with the 53-6.7 mAb, it should be clear that other antibodies to the CD8 antigen, e.g., binding to either the CD8a or CD8b epitopes or both, can be equally effective in depleting CD8+ T lymphocytes.

The inventors demonstrate the pharmacokinetics of a single bolus of anti-CD8 antibody in the plasma and spinal cord after a single intraperitoneal injection. The delay in disease onset and slowing of disease progression were measurable by two parameters, daily body weight measures, and daily measurements of neurological score.

In summary, anti-CD8 antibody treatment depletes cytotoxic CD8+ T cells after a single bolus injection. Treatment with anti-CD8 antibody decreases the expression of messenger RNAs that are associated with astrocyte and microglial activation in the spinal cord. The effect of depleting cytotoxic CD8+ T cell populations with an anti-CD8 antibody is to ameliorate disease in the mouse preclinical neurodegenerative ALS model. It is also reasonable that depleting CD8+ cytotoxic T cells may be advantageous in other neurodegenerative and neuromuscular disease indications such as Alzheimer's Disease, Parkinson's Disease, Amyotrophic Lateral Sclerosis, Myasthenia Gravis, Multifocal Motor Neuropathy, Primary Lateral Sclerosis, Spinal Muscular Atrophy, Kennedy's Disease, and Spinocerebellar Ataxia.

In some preferred embodiments, the compound of the present invention is administered in a pharmaceutically acceptable carrier. The phrase "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent. Pharmaceutically acceptable carriers include pharmaceutically acceptable salts, where the term "pharmaceutically acceptable salts" includes salts of the active compounds which are prepared with relatively nontoxic acids or bases, depending on the particular substituents found on the compounds described herein. Examples of pharmaceutically acceptable carriers are solvents, diluents, dispersion media, suspension aids, surface active agents, preservatives, solid binders, stabilizers, fillers, binding agents, lubricants, coatings, antibacterial and antifungal agents, isotonic and absorption delaying agents, and the like that are physiologically compatible. Various vehicles and carriers used in formulating pharmaceutical compositions and known techniques for the preparation thereof are disclosed in Remington's Pharmaceutical Sciences (A. Osol et al. eds., 15th ed. 1975). Pharmaceutically acceptable carriers may further comprise minor amounts of auxiliary substances such as wetting or emulsifying agents, preservatives or buffers, which enhance the shelf life or effectiveness of the pharmacological agent.

Such carriers enable the compounds of the invention to be formulated as tablets, pills, dragees, capsules, liquids, gels, syrups, slurries, suspensions and the like, for oral ingestion by a patient to be treated. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. In one embodiment, mannitol and magnesium stearate are used as pharmaceutically acceptable carriers.

In some preferred embodiments, the compound of the present invention is administered with and adjuvant. The term "adjuvant" can be a compound that lacks significant activity administered alone but can potentiate the activity of another therapeutic agent. In some embodiments, an adjuvant is selected from the group consisting of buffers, anti-microbial preserving agents, surfactants, antioxidants, tonic regulators, antiseptics, thickeners and viscosity improvers.

The pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. In one embodiment, the preferred mode of administration is oral delivery.

Various solid oral dosage forms can be used for administering compounds of the invention including such solid forms as tablets, gelcaps, capsules, caplets, granules, lozenges and bulk powders.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (I.e., the pharmacological agent) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The agent that depletes CD8+ T cells that are administered in the methods of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g., *Sustained and Controlled Release Drug Delivery Systems*, J. R. Robinson, ed., Marcel Dekker, Inc., New York, 1978; U.S. Pat. Nos. 6,333,051 to Kabanov et al., and 6,387,406 to Kabanov et al.).

Supplementary active compounds can also be incorporated into the compositions. In certain embodiments, the agent that depletes CD8+ T cells of the present invention is coformulated with and/or coadministered with one or more additional therapeutic agents that are useful for improving the pharmacokinetics of the pharmacological agent.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In one embodiment, an initial bolus dose followed by smaller maintenance doses is administered. It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. It is also noted that when the agent that depletes CD8+ T cells is administered along with another active agent, the dosage of one or both compounds may be decreased from the single-agent dose.

A mouse model for ALS is the SOD1 G93A mouse. The SOD1 G93A mouse model is a mouse that carries 25 copies of the human G93A SOD mutation and is driven by the endogenous promoter. Survival in the mouse is copy dependent. The high copy G93A has a median survival of around 128 days. High molecular weight complexes of mutant SOD protein are seen in the spinal cord beginning around day 30. At day 60 reactive astrocytosis (GFAP reactive) are observed; activated microglia are observed from day 90 onwards. Studies by Gurney et al. showed that at day 90 reactive astrocytosis loses statistical significance while microglial activation is significantly elevated and continues to be elevated through the end stage of the disease. Many drugs that have shown efficacy in this model have moved forward into human clinical trials. Experience with riluzole, the only approved drug in the treatment of ALS, indicates that the mouse ALS model is a good predictor of clinical efficacy. Other drugs such as Creatine, Celebrex, Co-enzyme Q10 are under clinical evaluation based on studies in this model.

As used herein, the term "subject" is a human or other animal, having a neurological disorder. Thus, in some embodiments the subject will be in need of the therapeutic treatment as provided herein. Preferred patients are mammals. Examples of patients include but are not limited to, humans, horses, monkeys, dogs, cats, mice, rates, cows, pigs, goats and sheep. In some embodiments, "subjects" are generally human patients having ALS.

The term "treatment" or "treating" as used herein is intended to encompass preventing the onset, slowing the progression, reversing or otherwise ameliorating a neurological disorder such as a neurodegenerative and/or neuromuscular disorder.

In some embodiments, the treatment does not significantly change or influence the CD4+ T cell population. In some embodiments the treatment will reduce the concentration of CD8+ T cells in whole blood by at least 20, 30, 40, 50, 60, 70, 80, 90 percent or more compared to the concentration in whole blood prior to administering the compound. In some embodiments the treatment will reduce the concentration of CD8+ T cells in spinal fluid by at least 20, 30, 40, 50, 60, 70, 80, 90 percent or more compared to the concentration in whole blood prior to administering the compound. In some embodiments, the treatment will decrease the expression of one or more pro-inflammatory genes in the spinal cord by at least 20, 30, 40, 50, 60, 70, 80, 90 percent or more compared to the expression of the pro-inflammatory gene in the spinal cord prior to the treatment. The before and after measurements can be made, for example, at 50 days after dosing.

The term "depleting" or "depletes" means reduces the concentration by at least 10, 20, 30, 40, 50, 60, 70, 80, 90 percent or more compared to the concentration prior to the depletion by, for example, sequestering or neutralization.

The term "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

As used herein and in the appended claims, the singular forms "a," "an," and "the," include plural referents unless the context clearly indicates otherwise. Thus, for example, reference to "a molecule" includes one or more of such molecules and reference to "the method" includes reference to equivalent steps and methods known to those of ordinary skill in the art that could be modified or substituted for the methods described herein.

EXAMPLES

Aspects of the applicant's teachings may be further understood in light of the following examples, which should not be construed as limiting the scope of the applicant's teachings in any way.

Example 1

Anti-CD8 T Cell-Depleting Antibodies in Wild Type and SOD1$^{G93A}$ Mice

In order to characterize the effects of a rat anti-CD8 antibody in depleting T cell populations, six SOD1$^{G93A}$ mice were injected with either a single bolus of anti-CD8 antibody or a rat IgG isotype control antibody by intraperitoneal injection. Animals were euthanized according to IACUUC protocols at either day 5 or day 13 after injection.

Figure 1B:
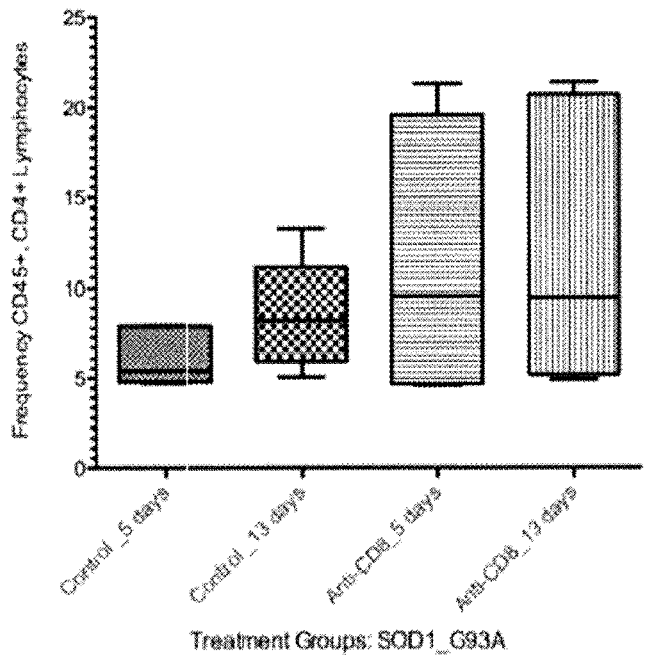
FIG. 1B is a graph of population levels of CD4+ T cells following exposure to treatment according to the invention or controls. Taken together.

Statistical analysis for cell count differences among treatment groups was performed using GraphPad Prism (v5). As can be seen in FIG. 1A there is a significant depletion of CD8+ T cells as early as 5 days after treatment with anti-CD8 T cell depleting antibody (p=0.0001). The effect of CD8+ T cell depletion was still evident after 13 days. As can be seen in FIG. 1B there was no statistically significant change detectable in CD4+ T cell populations after treatment with the anti-CD8 antibody (p=0.354).

Example 2

Characterization of Neuroinflammatory Markers in the Spinal cord after Anti-CD8 Antibody Treatment In order to characterize the impact of CD8+ T cell depletion in the central nervous system, spinal cords from anti-CD8-treated and IgG isotype control-treated SOD1$^{G93A}$ mice were harvested at age 100 days, i.e., 50 days after a single 300 μg intraperitoneal bolus injection of antibody was given. Spinal cords were fixed in 4% paraformaldehyde and embedded in paraffin for sectioning. ALS TDI has a collaboration with the Allen Brain Institute for in situ hybridization (ISH) analysis of gene expression in spinal cord. In the last three years ALS TDI has collected the expression patterns of more than 2000 genes in SOD spinal cords at ages 50 and 90 days. A panel of genes was indentified from this database of expression data that include markers of neurons, astrocytosis, and microglial activation. Among these genes, twenty-four were selected that provided a robust, reproducible signature of changes occurring in SOD1, compared to wild type mice. These were analyzed to assess the impact of anti-CD8 treatment on neuronal survival, astrocytosis, and microglial activation in treated and untreated SOD1$^{G93A}$ animals.

Figures 2A, 2B, 2C, 2D, 2E, 2F, 2G, 2H:
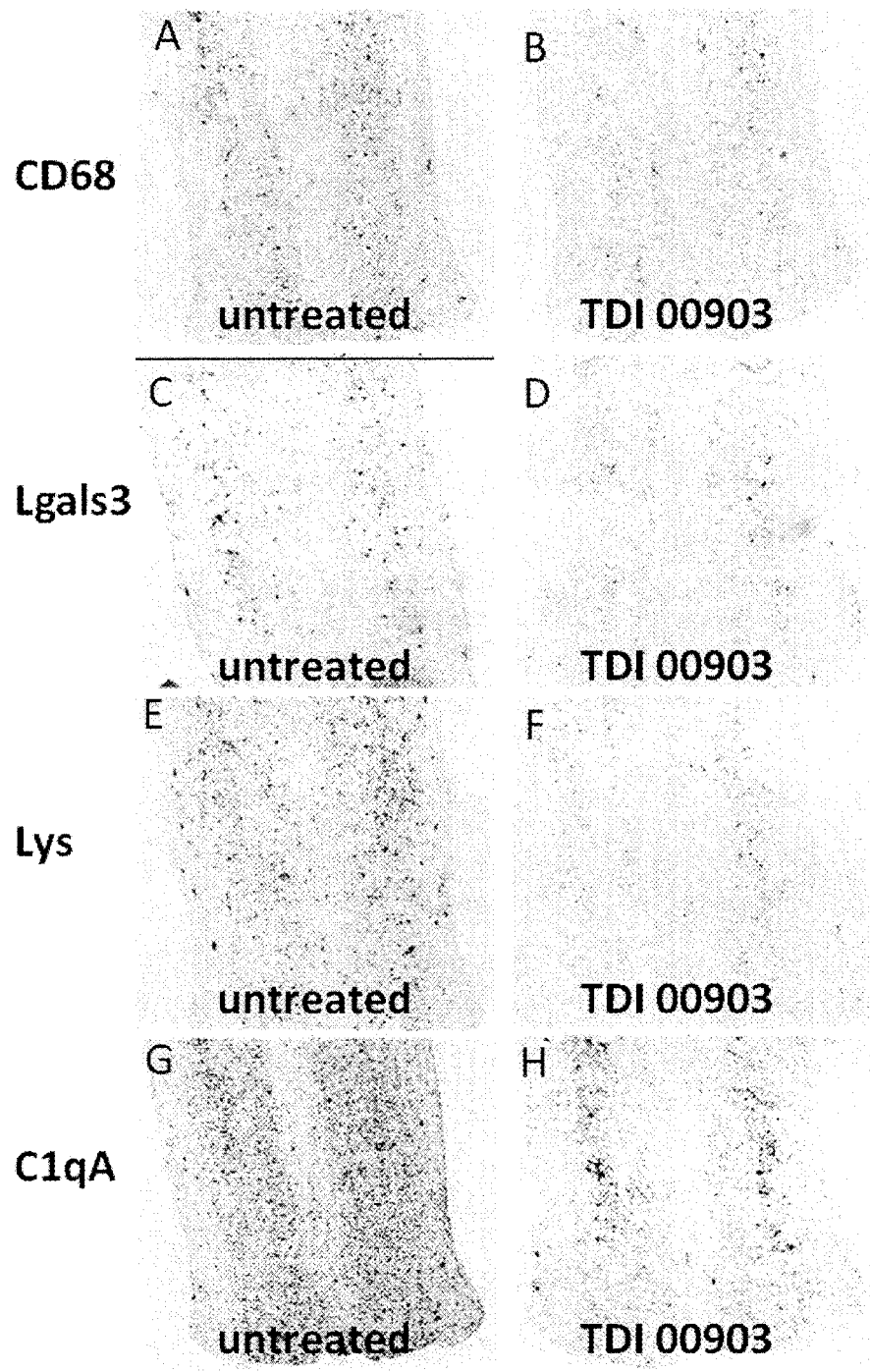
FIGS. 2A-2H are a series of images of in-situ hybridization (ISH) data for four 4 genes (CD68, Lgals3, Lys, and C1Q) obtained from lumbar spinal cord samples from treated (left column) and untreated (right column) mice. The images demonstrate that anti-CD8 treatment alters transcript localization patterns in the lumbar spinal cord.
Figures 3A, 3B, 3C, 3D:
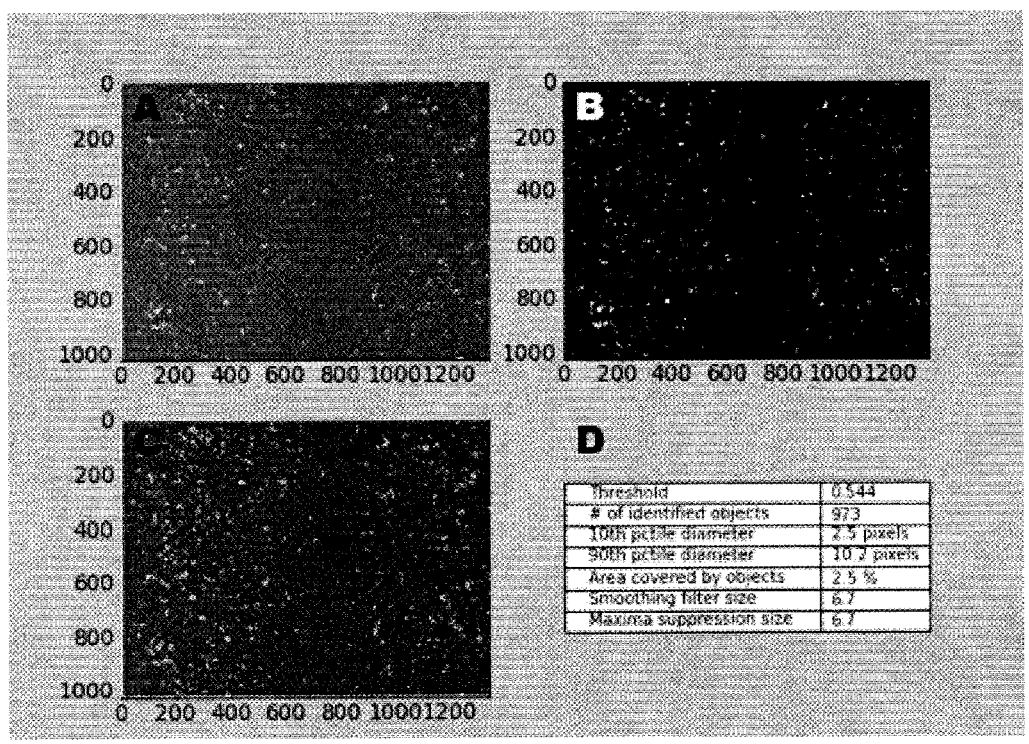
FIGS. 3A-3D presents a quantitative image analysis of the in situ hybridization (ISH) pattern for CD68 in the spinal cord of a vehicle control treated $SOD1^{G93A}$ mouse.
Figure 4A:
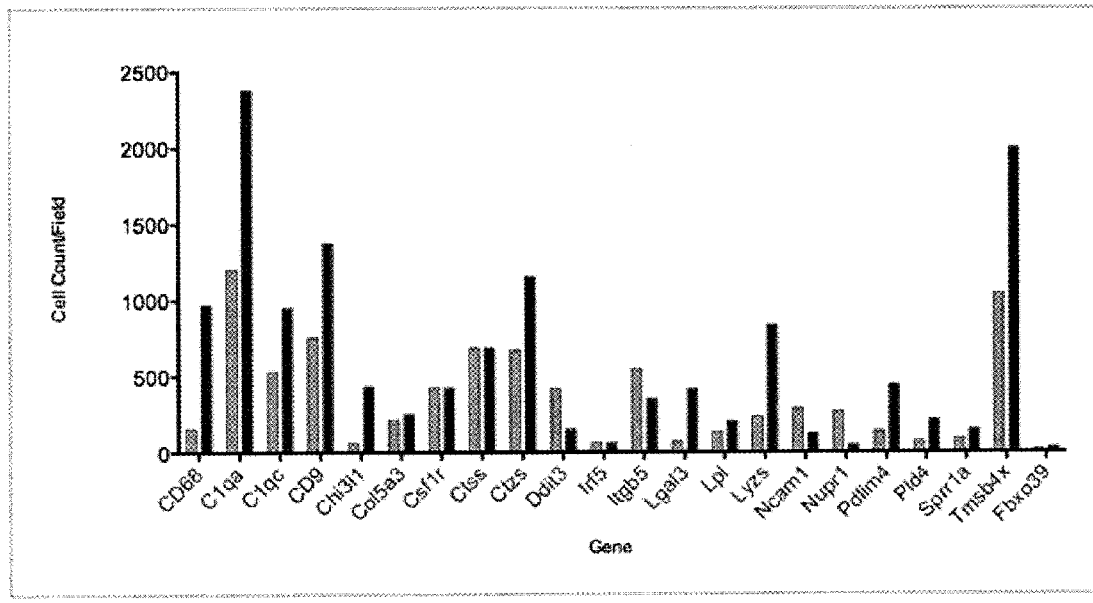
FIG. 4A presents quantified and normalized ISH data for 22 genes expressed in $SOD1^{G93A}$ spinal cord tissue.
Figure 4B:
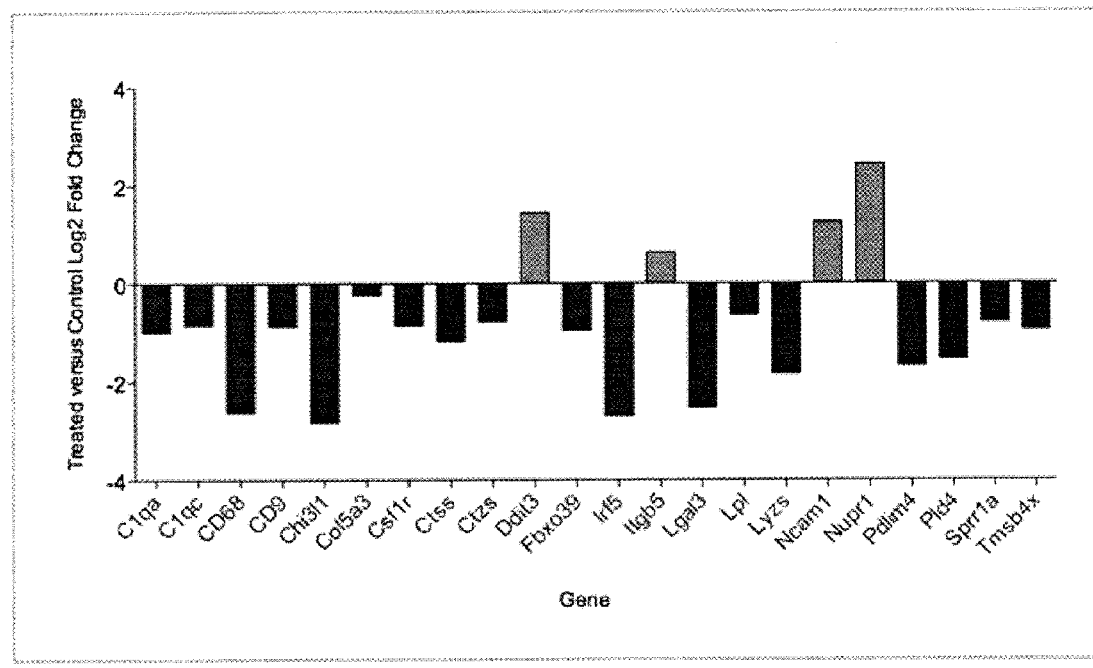
FIG. 4B is a graph of intensity ratios of expression for untreated and anti-CD8 treated genes in the lumbar spinal cord of $SOD1^{G93A}$ animals at 90 days of age.

In FIG. 2, a representative example of the ISH data from lumbar spinal cord at 100 days of age is shown for 4 genes (CD68, Lgals3, Lys, and C1Q) from treated and untreated SOD1$^{G93A}$ mice. There is a considerable decrease in signal intensity for these genes in the anti-CD8 treated group compared to control. In order to quantify these signals, an automated image analysis system was developed that counts the pixel intensities across fields to generate an average intensity for a given ISH section (FIGS. 3A-3D). The signal intensities for 22 genes in the lumbar spinal cord of SOD1$^{G93A}$ animals treated with either anti-CD8 T cell-depleting antibody or vehicle controls are shown in FIG. 4A. Grey columns are treated animals and black columns are untreated animals. The ratio of signal intensities shows that anti-CD8 treatment decreases the signal intensities for most of the makers in the panel of genes, with exception of four genes that show increased expression (FIG. 4B). The precise reason for the up-regulation of these four genes is unclear. However, it is interesting that two of the genes are involved in cell adhesion (ICAM, ITGB5) and two are involved in cellular stress signaling (Nupr1, ddit3).

Example 3

A Single Bolus Injection with an Anti-CD8 Lymphocyte-Depleting Antibody Trends Toward Delaying Disease Onset, Slowing Disease Progression, and Prolonging Survival in Female hSOD1$^{G93A}$ Mice, a Preclinical Animal Model of ALS The impact of depleting cytotoxic T cell populations on disease progression was assessed in the hSOD1$^{G93A}$ preclinical animal model. The goal of the experiment was to administer the anti-CD8 antibody to hSOD1$^{G93A}$ mice and assess parameters of disease progression, including daily measurements of body weight and neurological severity score, as well as to determine the effect of anti-CD8 treatment on survival. The experimental design assigned 16 female and 16 male hSOD1$^{G93A}$ mice to the anti-CD8 treatment group and 16 female and 16 male hSOD1$^{G93A}$ litter mates to the vehicle control group (Tables 1 & 2).

TABLE 1

| Study Design: Anti-CD8 Antibody Survival Efficacy Test in SOD1$^{G93A}$ Mice, Dosing at Age 50 Days | |
|---|---|
| Study Name: | CD8 Survival Efficacy Study day 50 start |
| Treatments Used: | CD8 |
| Species: | Mouse |
| Genotype: | SOD1(G93A)/+ |
| Strain: | B6SJL-TgN(SOD1-G93A)1Gur |
| Animals/Group: | Therapeutic: 32, Control: 32 |

TABLE 2

Study Groups: Anti-CD8 Antibody Survival Efficacy
Test in SOD1$^{G93A}$ Mice, Dosing at Age 50 Days

| Treatment Group | Control or Test Therapeutic | Females (Assigned/ Total) | Males (Assigned/ Total) | Litter Matched |
|---|---|---|---|---|
| Anti-CD8 Treatment | Test Therapeutic | 16/32 | 16/32 | Yes |
| Control Group | Control | 16/32 | 16/32 | Yes |

A single bolus IP injection of anti-CD8 antibody was given on the starting day of the study at age 50 days (Table 3). Animals were monitored daily throughout the course of the study. Body weight and neurological disease severity score were measured daily.

TABLE 3

Treatment Formulation and Dosing Regimen:
Anti-CD8 Antibody Survival Efficacy Test in SOD1$^{G93A}$ Mice
Dosing at Age 50 Days

| | |
|---|---|
| Treatment Name: | Anti-CD8 Antibody |
| Drug Source: | Taconic |
| Formulation Name: | 300 µg Loading Dose Formulation of □CD8 |
| Description: | 300 µg dose of anti-CD8 |
| Method of Formulation: | Add 2.727 mL of anti-CD8 to 270 µL of PBS. |
| Stability/Storage Handling: | Must be made fresh on the day of dosing. |
| Physical Form: | Liquid |
| Route: | Intraperitoneal (IP Injection) |
| Vehicle: | PBS |
| Dose: | 300 µg/injection |
| Frequency: | Single Bolus |
| Volume: | 200 µL |
| Dosing Rationale: | Deletion of CD8+ cytotoxic T cells |

Neurological scores for both hind legs were assessed daily for each mouse from 50 days of age. The neurological score employed a scale of 0 to 4 that was developed by observation at ALSTDI (Scott et al., 2008). Briefly, animals are assigned a score of 0 if they show full extension of their hind legs away from the lateral midline when the mouse is suspended by its tail, and the mouse can hold this position for 2 seconds, suspended 2-3 times. Animals are assigned a score of 1 when they display collapse or partial collapse of leg extension towards lateral midline (weakness) or trembling of hind legs during tail suspension. Animals are assigned a score of 2 when the toes curl under at least twice during walking a distance of 12 inches, or any part of the foot is dragging along the cage bottom/table. Animals are assigned a score of 3 when they have rigid paralysis or minimal joint movement, or a foot is not being used for forward motion. Animals are assigned a score of 4 when they cannot right themselves within 30 seconds after being laid on either side. At the point where at least one hind leg is scored as 2, food pellets are left on the cage bedding to permit easy access to food. If both hind legs are scored as 2, Nutra-Gel® (Bio-Serve #S4798) is provided as food in addition to food pellets placed on the cage bedding and a long sipper tube is placed on the water bottle.

Date and cause of death were recorded for each mouse. For humane reasons, animals are closely monitored and sacrificed as moribund prior to actual death using criteria for severe moribundity. To determine duration of survival reliably and humanely, the moribund state, defined as the inability of mice to right themselves 30 seconds after being placed on a side (a neurological score of 4) was used. The moribund mice were scored as "dead", and were euthanized using carbon dioxide.

Prior to statistical analysis animals dying non ALS-related deaths in both treatment and control groups were removed from subsequent analysis (Table 4).

TABLE 4

Survival Summary
Anti-CD8 Antibody Survival Efficacy Test in SOD1$^{G93A}$ Mice
Dosing at Age 50 Days

| Cause of Death | Group | Number of Animals |
|---|---|---|
| Total ALS Deaths (uncensored animals) | Control: | 31 |
| | Test Therapeutic: | 30 |
| Non ALS Death | Control: | 1 |
| | Test Therapeutic: | 2 |

In this case, 1 control animal and 2 anti-CD8-treated animals were removed due to non ALS-related death.

Mutant SOD1 transgenic animals display normal body weight (BW) characteristics as neonates and gain weight normally compared to nontransgenic animals into adulthood. Depending on the nature of the genetic mutation in the transgene, and the number of copies of the mutant transgene, animals begin to lose weight after symptom onset and weight loss continues until death. A retrospective analysis of weight loss in treatment and control groups can provide insight into putative treatment effects on disease onset and rate of progression. In order to assess the impact of anti-CD8 treatment on body weight two parameters were examined. First, changes in BW from initiation of study to the attainment of peak body weight are determined. These may reflect an impact on disease onset. Second, changes from peak body weight until death are also determined. These may reflect an impact on disease progression. Summary statistics for body weight measurements are presented in Table 5.

TABLE 5

Body Weight Statistics
Anti-CD8 Antibody Survival Efficacy Test in SOD1$^{G93A}$ Mice
Dosing at Age 50 Days
Indicators of Body Weight Maintenance

| | | Females | | | Males | | | Combined | | |
|---|---|---|---|---|---|---|---|---|---|---|
| Measure | Treatment | N | Mean | [95% C.I.] | N | Mean | [95% C.I.] | N | Mean | [95% C.I.] |
| Body Weight Change (g) | | | | | | | | | | |
| Max | CTRL | 16 | 2.5 | 1.9   3.0 | 16 | 2.9 | 2.3   3.6 | 32 | 2.7 | 2.3   3.1 |
| | DRUG | 16 | 2.7 | 2.3   3.1 | 16 | 2.2 | 1.7   2.8 | 32 | 2.5 | 2.1   2.8 |
| | Δ (D-C) | | +0.2 | | | −0.7 | | | −0.2 | |
| | P | | 0.48 | | | 0.10 | | | 0.38 | |

TABLE 5-continued

Body Weight Statistics
Anti-CD8 Antibody Survival Efficacy Test in SOD1$^{G93A}$ Mice
Dosing at Age 50 Days
Indicators of Body Weight Maintenance

| Measure | Treatment | Females | | | Males | | | Combined | | |
|---|---|---|---|---|---|---|---|---|---|---|
| | | N | Mean | [95% C.I.] | N | Mean | [95% C.I.] | N | Mean | [95% C.I.] |
| Min | CTRL | 16 | −1.6 | −2.2 −1.0 | 16 | −2.3 | −3.4 −1.1 | 32 | −1.9 | −2.6 −1.3 |
| | DRUG | 16 | −1.6 | −2.1 −1.0 | 16 | −3.6 | −4.3 −2.8 | 32 | −2.6 | −3.1 −2.0 |
| | Δ (D-C) | | +0.1 | | | −1.3 | | | −0.6 | |
| | P | | 0.88 | | | 0.05 | | | 0.14 | |
| Max-Min | CTRL | 16 | 4.1 | 3.5 4.7 | 16 | 5.2 | 3.9 6.5 | 32 | 4.6 | 3.9 5.3 |
| | DRUG | 16 | 4.2 | 3.7 4.8 | 16 | 5.8 | 5.2 6.4 | 32 | 5.0 | 4.5 5.5 |
| | Δ (D-C) | | +0.1 | | | +0.6 | | | +0.4 | |
| | P | | 0.71 | | | 0.36 | | | 0.36 | |
| Median | CTRL | 16 | 1.3 | 1.0 1.7 | 16 | 1.8 | 1.2 2.4 | 32 | 1.6 | 1.2 1.9 |
| | DRUG | 16 | 1.6 | 1.3 1.9 | 16 | 1.3 | 0.8 1.8 | 32 | 1.5 | 1.2 1.7 |
| | Δ (D-C) | | +0.3 | | | −0.5 | | | −0.1 | |
| | P | | 0.21 | | | 0.15 | | | 0.58 | |

Time (days)

| | | N | Mean | [95% C.I.] | N | Mean | [95% C.I.] | N | Mean | [95% C.I.] |
|---|---|---|---|---|---|---|---|---|---|---|
| Age at Max | CTRL | 16 | 93.6 | 87.5 99.6 | 16 | 98.1 | 92.7 103.5 | 32 | 95.8 | 91.9 99.7 |
| | DRUG | 16 | 98.3 | 92.1 104.6 | 16 | 89.1 | 82.0 96.1 | 32 | 93.7 | 88.9 98.4 |
| | Δ (D-C) | | +4.8 | | | −9.0 | | | −2.1 | |
| | P | | 0.25 | | | 0.04 | | | 0.48 | |
| Initial to Peak | CTRL | 16 | 43.6 | 37.5 49.6 | 16 | 48.1 | 42.7 53.5 | 32 | 45.8 | 41.9 49.7 |
| | DRUG | 16 | 48.3 | 42.1 54.6 | 16 | 39.1 | 32.0 46.1 | 32 | 43.7 | 38.9 48.4 |
| | Δ (D-C) | | +4.8 | | | −9.0 | | | −2.1 | |
| | P | | 0.25 | | | 0.04 | | | 0.48 | |
| Peak to Death | CTRL | 16 | 28.8 | 22.7 34.8 | 16 | 30.9 | 26.3 35.5 | 32 | 29.8 | 26.3 33.4 |
| | DRUG | 16 | 29.3 | 25.0 33.6 | 16 | 36.9 | 27.5 46.4 | 32 | 33.1 | 28.1 38.2 |
| | Δ (D-C) | | +0.6 | | | +6.0 | | | +3.3 | |
| | P | | 0.87 | | | 0.23 | | | 0.29 | |

Figures 5A, 5B, 5C:
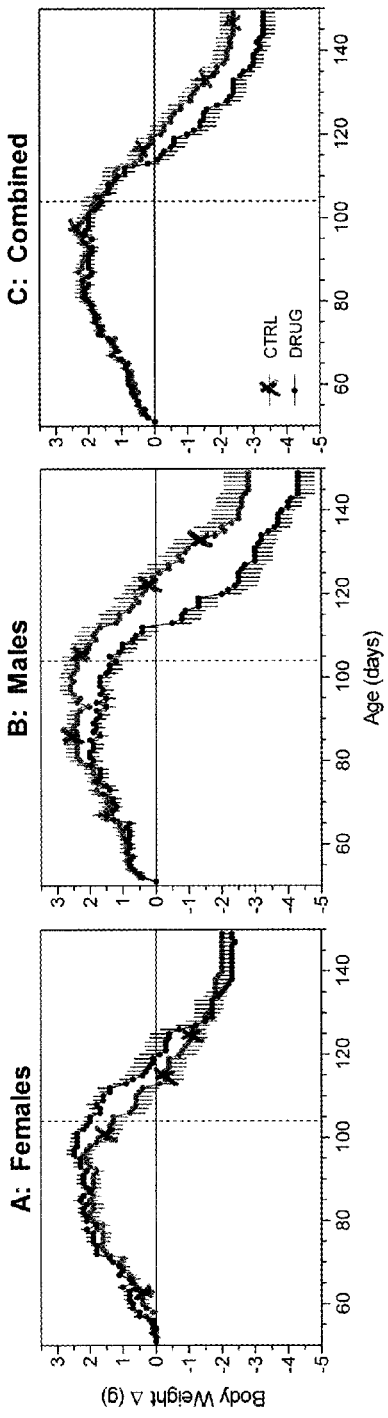
FIGS. 5A-5C are graphs of daily group average change from initial body weight over time (±SEM) from study start at age 50 days until death. Data for both animals in a saline control group and animals in an anti-CD8-treated group are provided.

Daily group average changes in body weight, from study start at age 50 days until the last death, are shown for the anti-CD8 treated and vehicle control groups in FIGS. 5A-5C where the different figures provide the female (5A), male (5B) subpopulations as well as the combined female and male population (5C). As animals die, last body weight change value is carried forward in this depiction.

Figures 6A, 6B, 6C:
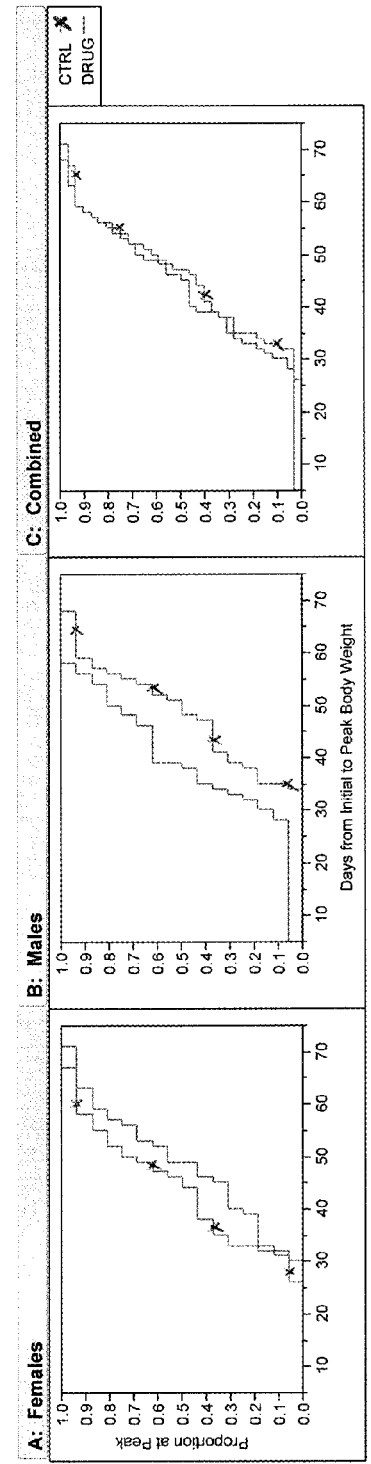
FIGS. 6A-6C are Kaplan-Meier time-to-event graphs for the number of days taken from initial to peak body weight. Data for both animals in a saline control group and animals in an anti-CD8-treated group are provided.

The anti-CD8-treated and vehicle control group time-to-event curves for the time from initial to peak body weight are shown in FIGS. 6A-6C. The median time to peak body weight for the control group was 47 days, compared to 46 days for the anti-CD8 treated group (Table 6). Kaplan-Meier nonparametric and Cox proportional hazard partly parametric analysis of the time from study initiation to peak BW showed no significant difference in anti-CD8-treated animals compared to saline injected animals using Log-Rank (K-M), Wilcoxon (K-M), and Likelihood Ratio (Cox PH) statistical tests (Table 6).

TABLE 6

K-M Product-Limit and Cox PH Fits of Time from Initial to Peak Body Weight
Anti-CD8 Antibody Survival Efficacy Test in SOD1$^{G93A}$ Mice
Dosing at Age 50 Days
Time from Initial to Peak Body Weight (days)

| Subjects | Group | N | Median | [95% C.I.] | Fit | Test | P |
|---|---|---|---|---|---|---|---|
| Females | CTRL | 16 | 45 | 33 49 | K-M | Log-Rank | 0.27 |
| | DRUG | 16 | 49 | 39 53 | | Wilcoxon | 0.27 |
| | Δ (D-C): | | +4 | | Cox | Likelihood | 0.27 |
| | Hazard Ratio [95% C.I.]: | | 0.66 | 0.32 1.38 | PH | Ratio | |
| Males | CTRL | 16 | 50 | 38 54 | K-M | Log-Rank | 0.06 |
| | DRUG | 16 | 39 | 32 46 | | Wilcoxon | 0.04 |
| | Δ (D-C): | | −11 | | Cox | Likelihood | 0.08 |
| | Hazard Ratio [95% C.I.]: | | 1.93 | 0.93 3.97 | PH | Ratio | |
| Combined | CTRL | 32 | 47 | 38 51 | K-M | Log-Rank | 0.85 |
| | DRUG | 32 | 46 | 35 49 | | Wilcoxon | 0.57 |
| | Δ (D-C): | | −2 | | Cox | Likelihood | 0.73 |
| | Hazard Ratio [95% C.I.]: | | 1.09 | 0.66 1.82 | PH | Ratio | |

Figures 7A, 7B, 7C:
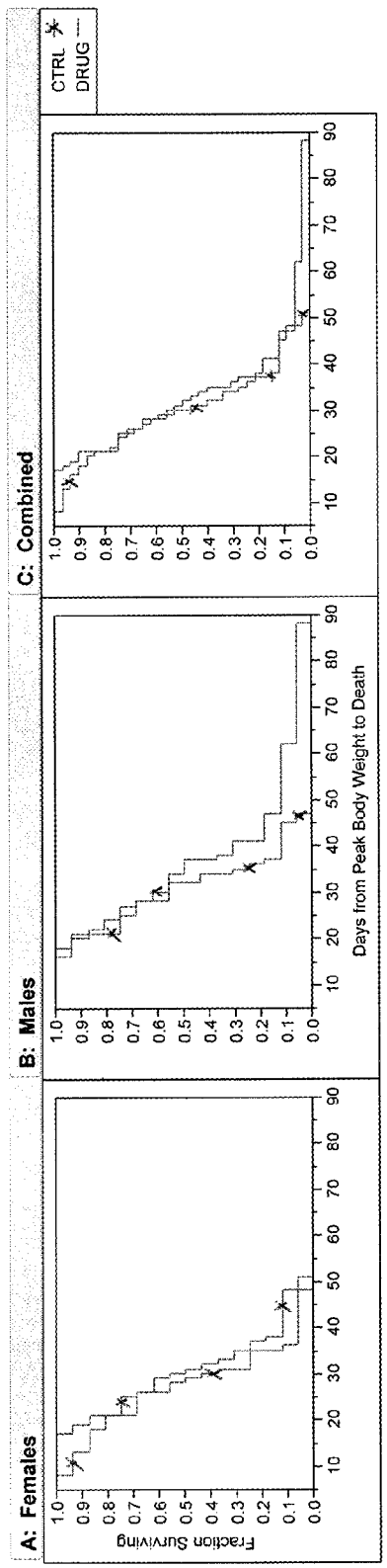
FIGS. 7A-7C are Kaplan-Meier time-to-event graphs for the number of days taken from the time of peak body weight until death. Data for both animals in a saline control group and animals in an anti-CD8-treated group are provided.

The anti-CD8-treated and vehicle control group time-to-event curves for the time from peak body weight until death are shown in FIGS. 7A-7C. The median time from peak body weight until death for the control group was 30 days, compared to 32 days for the anti-CD8 treated group (Table 7). Kaplan-Meier nonparametric and Cox proportional hazard partly parametric analysis of the time from study initiation to peak BW showed no significant difference in anti-CD8-treated animals compared to saline injected animals using Log-Rank (K-M), Wilcoxon (K-M), and Likelihood Ratio (Cox PH) statistical tests (Table 7).

TABLE 7

K-M Product-Limit and Cox PH Fits of Time from Peak Body Weight to Death:
Anti-CD8 Antibody Survival Efficacy Test in SOD1$^{G93A}$
Mice, Dosing at Age 50 Days
Time from Peak Body Weight to Death (days)

| Subjects | Group | N | Median | [95% C.I.] | | Fit | Test | P |
|---|---|---|---|---|---|---|---|---|
| Female | CTRL | 16 | 29 | 21 | 30 | K-M | Log-Rank | 0.84 |
| | DRUG | 16 | 31 | 21 | 33 | | Wilcoxon | 0.73 |
| | Δ (D-C): | | +2 | | | Cox | Likelihood | 0.85 |
| | Hazard Ratio [95% C.I.]: | | 1.07 | 0.52 | 2.20 | PH | Ratio | |
| Male | CTRL | 16 | 32 | 21 | 34 | K-M | Log-Rank | 0.17 |
| | DRUG | 16 | 36 | 24 | 38 | | Wilcoxon | 0.34 |
| | Δ (D-C): | | +4 | | | Cox | Likelihood | 0.19 |
| | Hazard Ratio [95% C.I.]: | | 0.61 | 0.29 | 1.27 | PH | Ratio | |
| Combined | CTRL | 32 | 30 | 26 | 32 | K-M | Log-Rank | 0.36 |
| | DRUG | 32 | 32 | 25 | 34 | | Wilcoxon | 0.49 |
| | Δ (D-C): | | +2 | | | Cox | Likelihood | 0.38 |
| | Hazard Ratio[95% C.I.]: | | 0.80 | 0.49 | 1.32 | PH | Ratio | |

Time-to-event analysis was also applied to the timing of the onset of definitive symptomatic neurological disease using the daily neurological scores of the saline-treated and anti-CD8 treated groups. On study start at age 50 days, all animals showed a neurological score of 0 with no observable symptoms or paralysis. Disease onset can be characterized by examining the progression in neurological score from a neurological score of 0 and 1 to a neurological score of 2 when animals are clearly dragging a hind limb.

Figures 8A, 8B, 8C:
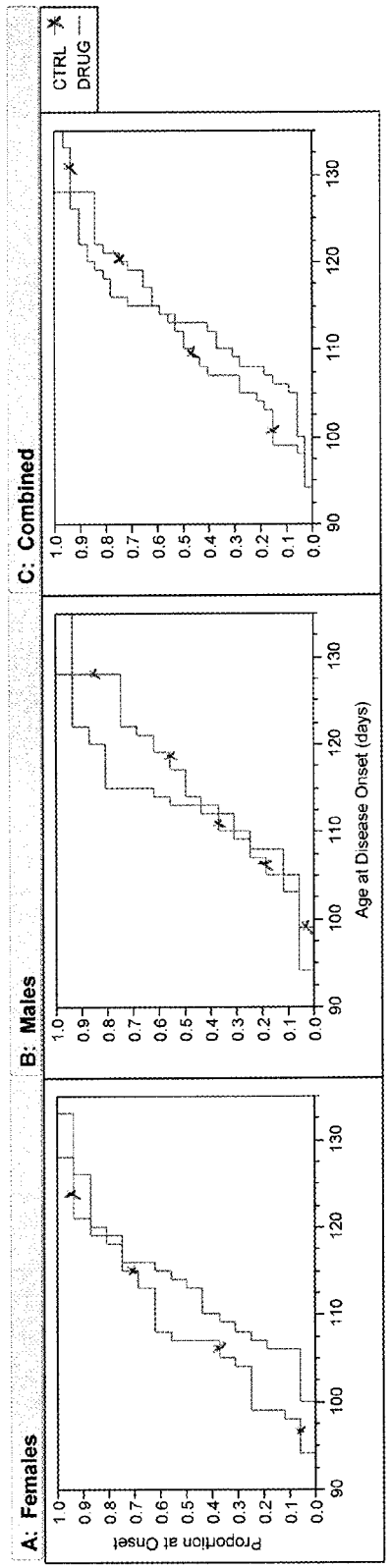
FIGS. 8A-8C are Kaplan-Meier time-to-event graphs for the age at onset of definitive neurological disease. Data for both animals in a saline control group and animals in an anti-CD8-treated group are provided.

The anti-CD8-treated and vehicle control group time-to-event curves for the age at onset of definitive neurological disease (score 2) are shown in FIG. 8. A gender difference was apparent in the time of disease onset. In females, control group animals showed a median age at disease onset of 107 days. Anti-CD8-treated mice showed a median age at disease onset of 114 days, 7 days later than controls (Table 8).

TABLE 8

K-M Product-Limit and Cox PH Fits of Time to Onset of Definitive Neurological Disease
Anti-CD8 Antibody Survival Efficacy Test in SOD1$^{G93A}$ Mice
Dosing at Age 50 Days
Age at Onset of Definitive Neurological Disease (days)

| Subjects | Group | N | Median | [95% C.I.] | | Fit | Test | P |
|---|---|---|---|---|---|---|---|---|
| Female | CTRL | 16 | 107 | 99 | 113 | K-M | Log-Rank | 0.60 |
| | DRUG | 16 | 114 | 107 | 115 | | Wilcoxon | 0.17 |
| | Δ (D-C): | | +7 | | | Cox | Likelihood | 0.47 |
| | Hazard Ratio [95% C.I.]: | | 0.76 | 0.36 | 1.60 | PH | Ratio | |
| Male | CTRL | 16 | 116 | 107 | 121 | K-M | Log-Rank | 0.22 |
| | DRUG | 16 | 113 | 108 | 114 | | Wilcoxon | 0.50 |
| | Δ (D-C): | | -3 | | | Cox | Likelihood | 0.25 |
| | Hazard Ratio [95% C.I.]: | | 1.56 | 0.73 | 3.35 | PH | Ratio | |
| Combined | CTRL | 32 | 111 | 107 | 117 | K-M | Log-Rank | 0.55 |
| | DRUG | 32 | 113 | 109 | 114 | | Wilcoxon | 0.64 |
| | Δ (D-C): | | +2 | | | Cox | Likelihood | 0.99 |
| | Hazard Ratio [95% C.I.]: | | 0.99 | 0.58 | 1.71 | PH | Ratio | |

Kaplan-Meier nonparametric and Cox proportional hazard partly parametric analysis of age at disease onset showed no significant difference in anti-CD8-treated animals compared to saline injected animals using Log-Rank (K-M) and Likelihood Ratio (Cox PH) statistical tests. However, the Wilcoxon (K-M) test, which is more sensitive to differences that occur early in the time course, tended toward statistical significance (p=0.17, Table 8). Females showed the greatest lag in disease onset early in the time course shown in FIG. 8.

Although statistical analysis indicated that this difference in age at disease onset is not statistically significant after a single dose of anti-CD8 antibody given at 50 days of age, chronic dosing with anti-CD8 could prove to be more efficacious. After a single dose at age 50 days, CD8+ T cells repopulate by approximately 21 days after dosing and these repopulated CD8+ T cells have the potential to be toxic to SOD1$^{G93A}$ animals by 90 days of age. When males and females are combined, the positive trend in females after a single dose of anti-CD8 antibody is also offset by a later, slightly negative effect seen in males. However, vehicle-treated or untreated male SOD1$^{G93A}$ mice show earlier disease onset and earlier death than females as a matter of course. In this respect, dosing at age 50 days occurs at a later point in disease progression for males than it does for females, i.e., females began treatment at a less advanced stage in their disease. Earlier treatment initiation and more chronic treatment may prove to be more efficacious than giving a single dose of anti-CD8 antibody at age 50 days.

Figures 9A, 9B, 9C:
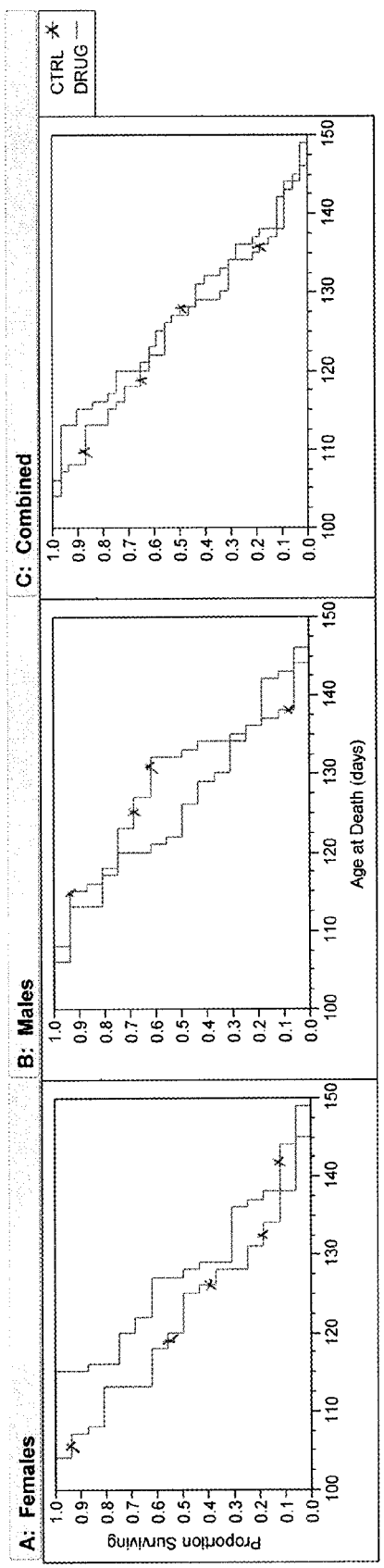
FIGS. 9A-9C are Kaplan-Meier time-to-event graphs for survival. Data for both animals in a saline control group and animals in an anti-CD8-treated group are provided.

There was also a gender difference with respect to anti-CD8 antibody treatment's effect on survival (age at death). Females showed a trend toward improved survival, particularly early in the time course (FIG. 9). Control group female showed a median survival age of 123 days; anti-CD8-treated females showed a median survival age of 128 days, a 5-day prolongation of survival (Table 9). When males and females are combined, the positive trend in females is offset by a negative impact on survival in male animals, where the control group males showed a median survival age of 133 days and the anti-CD8 treated males showed a median survival age of 124 days. Neither trend was statistically significant (Table 9).

TABLE 9

K-M Product-Limit and Cox PH Fits of Survival
Anti-CD8 Antibody Survival Efficacy Test in SOD1$^{G93A}$ Mice
Dosing at Age 50 Days
Survival: Age at Death (days)

| Subjects | Group | N | Median | [95% C.I.] | | Fit | Test[1] | P |
|---|---|---|---|---|---|---|---|---|
| Female | CTRL | 16 | 123 | 113 | 126 | K-M | Log-Rank | 0.28 |
| | DRUG | 16 | 128 | 116 | 129 | | Wilcoxon | 0.14 |
| | Δ (D-C): | | +5 | | | Cox | Likelihood | 0.25 |
| | Hazard Ratio [95% C.I.]: | | 0.65 | 0.31 | 1.35 | PH | Ratio | |
| Male | CTRL | 16 | 133 | 118 | 134 | K-M | Log-Rank | 0.59 |
| | DRUG | 16 | 124 | 117 | 130 | | Wilcoxon | 0.40 |
| | Δ (D-C): | | −9 | | | Cox | Likelihood | 0.58 |
| | Hazard Ratio [95% C.I.]: | | 1.23 | 0.60 | 2.53 | PH | Ratio | |
| Combined | CTRL | 32 | 128 | 118 | 132 | K-M | Log-Rank | 0.76 |
| | DRUG | 32 | 127 | 120 | 129 | | Wilcoxon | 0.72 |
| | Δ (D-C): | | −1 | | | Cox | Likelihood | 0.72 |
| | Hazard Ratio [95% C.I.]: | | 0.91 | 0.55 | 1.51 | PH | Ratio | |

[1]Testing Terms: In Kaplan-Meier (K-M) analysis the Log-Rank test places more weight on later event times; the Wilcoxon test places more weight on early event times and is the optimum rank test if the error distribution is logistic. P lists the probability of obtaining, by chance alone, a Chi-square value greater than the one computed if the time-to-event functions are the same for all groups. In Cox proportional hazards (Cox PH) analysis a Risk Ratio of 1.00 occurs when timing is likely identical in the two groups. The Effect Likelihood Test is the likelihood-ratio Chi-square test on the null hypothesis that the parameter estimate for the Treatment covariate is zero (no effect of treatment).

Figures 10A, 10B, 10C:
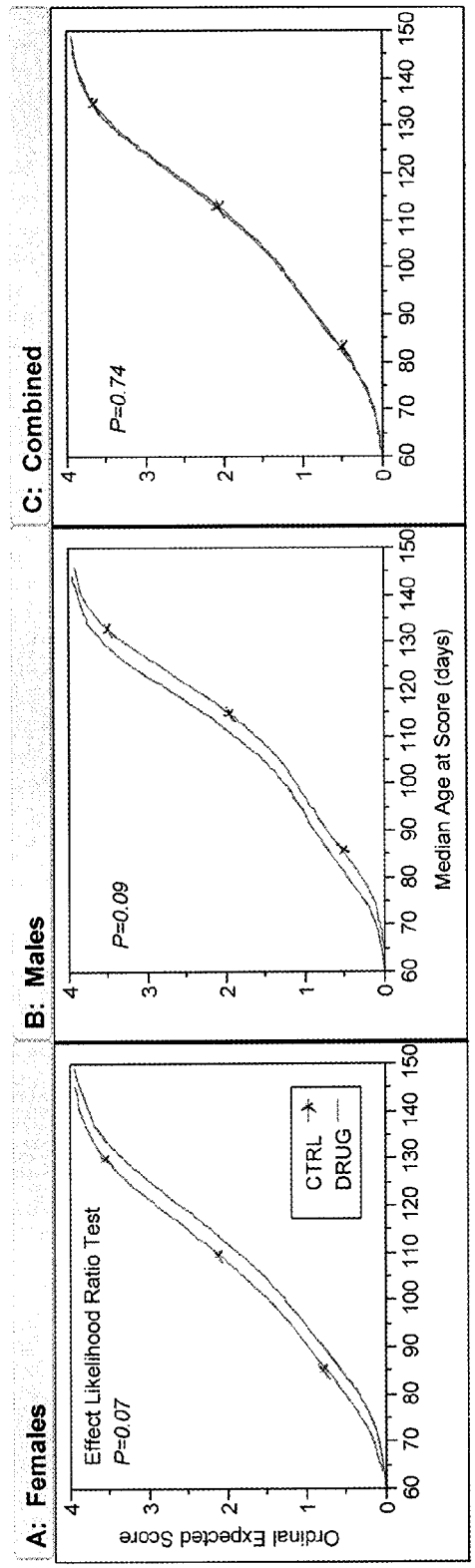
FIGS. 10A-10C are graphs of the rate of neurological disease progression over time. Ordinal logistic regression of neurological severity score by median age at score. Data for both animals in a saline control group and animals in an anti-CD8-treated group are provided.

In addition, anti-CD8-treated females showed a delay in neurological severity score progression when compared to controls (p=0.07, FIG. 10). Anti-CD8-treated males showed an earlier initiation in neurological score progression compared to controls. When males and females are combined, the positive trend in females is offset by a negative impact on neurological severity score progression in male animals. However, earlier treatment initiation and more chronic treatment may prove to be more efficacious than giving a single dose of anti-CD8 antibody at age 50 days.

Example 4

Production of Antibodies, Antibody Fragments and Immunoconjugates

Rodent monoclonal antibodies to available antigens can be obtained by methods known to those skilled in the art. See generally, for example, Kohler and Milstein, Nature 256:495 (1975), and Coligan et al. (eds.), CURRENT PROTOCOLS IN IMMUNOLOGY, VOL. 1, pages 2.5.1-2.6.7 (John Wiley & Sons 1991) ["Coligan"]. Briefly, monoclonal antibodies can be obtained by injecting mice with a composition comprising the antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen that was injected, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Suitable amounts of well-characterized antigen for production of antibodies can be obtained using standard techniques. As an example, CD8+ can be immunoprecipitated from B-lymphocyte protein using the deposited antibodies described by Tedder et al., U.S. Pat. No. 5,484,892 (1996). Alternatively, antigen proteins can be obtained from transfected cultured cells that overproduce the antigen of interest. Expression vectors that comprise DNA molecules encoding each of these proteins can be constructed using published nucleotide sequences. See, for example, Wilson et al, J. Exp. Med. 173:137 (1991); Wilson et al, J. Immunol. 150:5013 (1993). DNA molecules encoding the antigen of interest can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., Gene 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize genes as large as 1.8 kilobases in length. Adang et al, Plant Molec. Biol. 21:1131 (1993); Bambot et al., PCR Methods and Applications 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993).

In an alternative embodiment, an antibody of the present invention can be a chimeric antibody in which the variable regions of a human antibody have been replaced by the variable regions of a rodent antibody. The advantages of chimeric antibodies include decreased immunogenicity and increased in vivo stability.

Techniques for constructing chimeric antibodies are well known to those of skill in the art. As an example, Leung et al., Hybridoma 13:469 (1994), describe how they produced an LL2 chimera by combining DNA sequences encoding the $V_K$ and $V_H$ domains of LL2 monoclonal antibody with respective human κ and IgG1 constant region domains. This publication also provides the nucleotide sequences of the LL2 light and heavy chain variable regions, $V_K$ and $V_H$, respectively.

In another embodiment, an antibody of the present invention is a subhuman primate antibody. General techniques for raising therapeutically useful antibodies in baboons may be found, for example, in Goldenberg et al., international patent publication No. WO 91/11465 (1991), and in Losman et al., Int J Cancer 46: 310 (1990).

In yet another embodiment, an antibody of the present invention is a "humanized" monoclonal antibody. That is, mouse complementarity determining regions (CDRs) are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., Proc Nat'l Acad Sci USA 86:3833 (1989). Techniques for producing humanized monoclonal antibodies are described, for example, by Jones et al., Nature 321:522 (1986), Riechmann et al., Nature 332:323 (1988), Verhoeyen et al., Science 239:1534 (1988), Carter et al., Proc. Nat'l Acad. Sci. USA 89:4285 (1992), Sandhu, Crit. Rev Biotech. 12:437 (1992), and Singer et al., J Immun 150:2844 (1993). The publication of Leung et al., Mol Immunol 32:1413 (1995), describes the construction of humanized LL2 antibody.

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int Immun 6:579 (1994).

A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g., Johnson and Chiswell, Current Opinion in Structural Biology, 3:5564-571 (1993).

Although xenogeneic antibodies may be used in the invention, it is preferable to use allogeneic antibodies to reduce the likelihood of the antibodies themselves inducing an immune response from the host. In a particular embodiment of the invention, a human antibody is used. Methods for making fully human antibodies for use in human subjects include the use of phage display techniques for selecting antigen specific antibodies from a large human antibody library, as described in U.S. Pat. No. 5,969,108, which is incorporated herein by reference in its entirety. Other phage display methods for making human antibodies from designed human antibody libraries are described in U.S. Pat. No. 6,300,064, which is incorporated herein by reference in its entirety. See also: Marks, et al. "By-Passing Immunization: Building High Affinity Human Antibodies by Chain Shuffling." (Bio/Technology, vol. 10: p. 779-783. (1992)), Hoogenboom, et al. "Building Antibodies From Their Genes." (Rev Fr Transfus Hemobiol, vol. 36: p. 19-47, (1993)); Griffiths, et al. "Isolation of High Affinity Human Antibodies Directly from Large Synthetic Repertoires." EMBO J, vol. 13: p. 3245-3260 (1994)); Winter and Milstein "Man-Made Antibodies." (Nature, vol. 349: p. 293-299 (1991)); De Kruif, et al., "Selection and Application of Human Single Chain Fv Antibody Fragments from a Semi-synthetic Phage Antibody Display Library with Designed CDR3 Regions," (J Mol Biol, vol. 248, pp. 97-105 (1995)) and Barbas et al., "Semisynthetic combinatorial antibody libraries: A chemical solution to the diversity problem," (Proc Natl Acad. Sci. USA, vol. 89, pp. 4457-4461 (1992)).

Other methods for making fully human antibodies include the use of so-called "xenomouse" technology, using transgenic mice that encode a large portion of the human antibody repertoire. These methods are provided commercially by, for example, Abgenix (Fremont Calif.) and Medarex (Princeton N.J.). See also, U.S. Pat. No. 6,075,181; Lonberg, "Transgenic Approaches to Human Monoclonal Antibodies." Handbook of Experimental Pharmacology 113 (1994): 49-101; Lonberg et al. "Human Antibodies from Transgenic Mice." Internal Review of Immunology 13 (1995): 65-93.

The present invention encompasses antibodies and antibody fragments. Antibodies are generally bivalent, or less often multivalent, and this bivalency enhances the strength of attachment of the antibody to cell surfaces. However, the bivalency of the antibody sometimes induces a target cell to undergo antigenic modulation thereby providing a means whereby the cell can avoid the cytotoxic agents, effector cells and complement, which are involved in the cell-antibody interaction. As a means of preventing such modulation, monovalent antibodies or antibody fragments can be used. A monovalent antibody is a complete, functional immunoglobulin molecule in which only one of the light chains binds to antigen. One method of preparing such antibodies is disclosed in U.S. Pat. No. 4,841,025.

Monovalency can be achieved by using antibody fragments. Exemplary monovalent antibody fragments useful in these embodiments are Fv, Fab, Fab' and the like. Monovalent antibody fragments, typically exhibiting a molecular weight ranging from about 25 kD (Fv) to about 50 kD (Fab, Fab'), are smaller than whole antibody and, therefore, are generally capable of greater target site penetration. Moreover, monovalent binding can result in less binding carrier restriction at the target surface (occurring during use of bivalent antibodies, which bind strongly and adhere to target cell sites thereby creating a barrier to further egress into sublayers of target tissue), thereby improving the homogeneity of targeting. In addition, smaller molecules are more rapidly cleared from a recipient, thereby decreasing the immunogenicity of the administered small molecule conjugate. A lower percentage of the administered dose of a monovalent fragment conjugate localizes to target in comparison to a whole antibody conjugate. The decreased immunogenicity may permit a greater initial dose of the monovalent fragment conjugate to be administered, however. In addition, monovalent antibody fragments generally do not reside as long on the target cell as do bivalent or whole antibodies.

The antibody fragments are antigen binding portions of an antibody, such as F(ab')2, F(ab)$_2$, Fab', Fab, and the like. The antibody fragments bind to the same antigen that is recognized by the intact antibody. For example, an anti-CD8+ monoclonal antibody fragment binds to an epitope of CD8+ T cells.

As noted above, the term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the hypervariable region.

Multispecific antibodies and antagonists can be formed by engineering recombinant fusion proteins linking two or more different single-chain antibody or antibody fragment segments with the needed multiple specificities. See, e.g., Coloma et al., Nature Biotech 15:159-163, 1997. For example, a variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Functional bispecific single-chain antibodies (bscAb), also called diabodies, can be produced in mammalian cells using recombinant methods. See, e.g., Mack et al., Proc Natl Acad Sci, 92:7021-7025, 1995. For example, bscAb are produced by joining two single-chain Fv fragments via a glycine-serine linker using recombinant methods. The V light-chain ($V_L$) and V heavychain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the (Gly4-Ser1)$_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into a eukaryotic expression vector. Functional protein expression can be obtained by transfecting the vector into Chinese hamster ovary cells. Recombinant methods can be used to produce a variety of fusion proteins.

Any of the multispecific antagonists of the present invention can be conjugated with one or more therapeutic or diagnostic/detection agents. Generally, one therapeutic or diagnostic/detection agent is attached to each antibody, fusion protein or fragment thereof but more than one therapeutic agent and/or diagnostic/detection agent can be attached to the same antibody or antibody fragment. If the Fc region is absent (for example when the antibody used as the antibody component of the immunoconjugate is an antibody fragment), it is possible to introduce a carbohydrate moiety into the light chain variable region of a full length antibody or antibody fragment. See, for example, Leung et al., J Immunol 154: 5919 (1995); Hansen et al., U.S. Pat. No. 5,443,953 (1995), Leung et al., U.S. Pat. No. 6,254,868. The engineered carbohydrate moiety is used to attach the therapeutic or diagnostic/detection agent.

Methods for conjugating peptides to antibody components via an antibody carbohydrate moiety are well-known to those of skill in the art. See, for example, Shih et al., Int Cancer 41: 832 (1988); Shih et al., Int J Cancer 46: 1101 (1990); and Shih et al., U.S. Pat. No. 5,057,313. The general method involves reaction of an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

A therapeutic or diagnostic/detection agent can be attached at the hinge region of a reduced antibody component via disulfide bond formation. As an alternative, such agents can be attached to the antibody component using a heterobifunctional cross-linker, such as N-succinyl 3-(2-pyridyldithio) proprionate (SPDP). Yu et al., Int J Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic/detection agent can be conjugated via a carbohydrate moiety in the Fc region of the antibody. The carbohydrate group can be used to increase the loading of the same agent that is bound to a thiol group, or the carbohydrate moiety can be used to bind a different peptide.

One skilled in the art will appreciate further features and advantages of the invention based on the above-described embodiments. Accordingly, the invention is not to be limited by what has been particularly shown and described, except as indicated by the appended claims. All references, patents, patent applications and other publications cited herein are expressly incorporated herein in their entirety.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method of ameliorating Amyotrophic lateral sclerosis (ALS) in a subject with ALS, the method consisting essentially of:
   administering a therapeutically effective amount of an antibody to the subject, wherein the antibody depletes CD8+T cells present in the subject.

2. The method of claim 1 wherein the antibody comprises an antibody that binds to CD8+T cells.

3. The method of claim 2 wherein the antibody comprises a full length IgG.

4. The method of claim 2 wherein the antibody comprises a FAb fragment of an antibody.

5. The method of claim 2 wherein the antibody is a human or humanized antibody.

6. The method of claim 1 wherein the antibody is administered as a single dose.

7. The method of claim 1 wherein the antibody is administered in multiple doses.

8. The method of claim 1, wherein the antibody is administered in a composition wherein the composition further comprises a pharmaceutically acceptable carrier or adjuvant.

9. The method of claim 1, wherein administering the antibody reduces the concentration of CD8+T cells in whole blood by at least 30 percent compared to the concentration in whole blood prior to administering the compound.

10. The method of claim 1, wherein administering the antibody reduces the concentration of CD8+T cells in spinal fluid by at least 30 percent compared to the concentration in spinal fluid prior to administering the compound.

11. The method of claim 1, wherein administering the antibody reduces the expression of one or more pro-inflammatory genes in the subject's spinal cord by at least 50 percent compared to the concentration in the spinal cord prior to administering the compound.

12. The method of claim 1, wherein the subject is a human subject.

13. A method of ameliorating Amyotrophic lateral sclerosis (ALS) in a subject with ALS, the method consisting essentially of:

administering a therapeutically effective amount of an antibody that binds to CD8+T cells to the subject.

14. The method of claim 13, wherein the antibody comprises a full length IgG.

15. The method of claim 13, wherein the antibody comprises a FAb fragment of an antibody.

16. The method of claim 13, wherein the antibody is a human or humanized antibody.

17. The method of claim 13, wherein the antibody that binds to CD8+ T cells does not significantly bind to CD4+T cells.

* * * * *